US005607946A

United States Patent [19]

Kulagowski et al.

[11] Patent Number: 5,607,946
[45] Date of Patent: Mar. 4, 1997

[54] QUINOLONE DERIVATIVES AS DOPAMINE $D_4$ LIGANDS

[75] Inventors: Janusz J. Kulagowski, Bishops Stortford; Paul D. Leeson, Cambridge; Ian M. Mawer, Bishops Stortford, all of Great Britain

[73] Assignee: Merck Sharp & Dohme Ltd., Hoddesdon, England

[21] Appl. No.: 549,759

[22] PCT Filed: Feb. 25, 1994

[86] PCT No.: PCT/GB94/00383

§ 371 Date: Aug. 30, 1995

§ 102(e) Date: Aug. 30, 1995

[87] PCT Pub. No.: WO94/20471

PCT Pub. Date: Sep. 15, 1994

[30] Foreign Application Priority Data

Mar. 5, 1993 [GB] United Kingdom .................. 9304525
Aug. 5, 1993 [GB] United Kingdom .................. 9316261

[51] Int. Cl.⁶ ..................... A61K 31/47; C07D 215/227; C07D 215/12
[52] U.S. Cl. ........................... 514/312; 546/157; 544/363; 514/253
[58] Field of Search ............................ 546/157; 514/312, 514/253; 544/363

[56] References Cited

U.S. PATENT DOCUMENTS

| 3,514,459 | 5/1970 | Ritter | 546/157 |
| 3,799,928 | 3/1974 | Sclager | 546/157 |
| 5,064,837 | 11/1991 | McCombie | 514/312 |
| 5,318,971 | 6/1994 | McCombie | 514/254 |

FOREIGN PATENT DOCUMENTS

| 0364327 | 11/1988 | European Pat. Off. . |
| 64-63518 | 3/1989 | Japan . |

OTHER PUBLICATIONS

Portlock, J Org Chem, vol. 38, No. 13, pp. 2351–2355, 1973.

*Primary Examiner*—C. Warren Ivy
*Assistant Examiner*—D. Margaret M. Mach
*Attorney, Agent, or Firm*—Robert J. North; Melvin Winokur

[57] ABSTRACT

A class of chemical compounds comprising a 2(1H)-quinolone moiety and a substituted heterocyclic moiety, linked via the 3-position of the 2(1H)-quinolone moiety by a methylene group, are antagonists of dopamine receptor subtypes within the brain, having a selective affinity for the dopamine D4 receptor subtype over other dopamine receptor subtypes, and are accordingly of benefit in the treatment and/or prevention of psychotic disorders such as schizophrenia whilst manifesting fewer side-effects than those associated with classical neuroleptic drugs.

18 Claims, No Drawings

QUINOLONE DERIVATIVES AS DOPAMINE D₄ LIGANDS

This application is a 371 of PCT/GB 94/00385, filed 25 Feb. 1994.

This invention relates to the use of a particular class of heteroaromatic compounds. More particularly, the invention is concerned with the use of substituted 2(1H)-quinolone derivatives which are antagonists of dopamine receptor subtypes within the brain and are therefore of benefit in the treatment and/or prevention of psychotic disorders such as schizophrenia.

The "dopamine hypothesis" of schizophrenia predicts an increased activity of dopamine neurotransmission in the disease. The hypothesis is supported by early observations that drugs, such as amphetamine, with dopamine agonist or dopamine-releasing properties are capable of eliciting a psychosis indistinguishable from acute paranoid schizophrenia.

Schizophrenia is a disorder which is conventionally treated with drugs known as neuroleptics. In the majority of cases, the symptoms of schizophrenia can be treated successfully with so-called "classical" neuroleptic agents such as haloperidol. Classical neuroleptics generally are antagonists at dopamine $D_2$ receptors. The fact that classical neuroleptic drugs have an action on dopamine receptors in the brain thus lends credence to the "dopamine hypothesis" of schizophrenia.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., *Nature* (London), 1991, 350, 610) and $D_5$ (Sunahara et al., *Nature* (London), 1991, 350, 614) receptor subtypes have been described.

Notwithstanding their beneficial antipsychotic effects, classical neuroleptic agents such as haloperidol are frequently responsible for eliciting acute extrapyramidal symptoms and neuroendocrine disturbances. These side-effects, which clearly detract from the clinical desirability of classical neuroleptics, are believed to be attributable to $D_2$ receptor blockade in the striatal region of the brain. It is considered (Van Tol et al., supra) that compounds which can interact selectively with the dopamine $D_4$ receptor subtype, whilst having a less-pronounced action at the $D_2$ subtype, might be free from, or at any rate less prone to, the side-effects associated with classical neuroleptics, whilst at the same time maintaining a beneficial level of antipsychotic activity.

The compounds of use in the present invention, being antagonists of dopamine receptor subtypes within the brain, are accordingly of benefit in the treatment and/or prevention of psychotic disorders such as schizophrenia. Moreover, the compounds of use in the invention have a selective affinity for the dopamine $D_4$ receptor subtype over other dopamine receptor subtypes, in particular the $D_2$ subtype, and can therefore be expected to manifest fewer side-effects than those associated with classical neuroleptic drugs.

JP-A-64-63518 and HU-A-T/54348 variously describe certain 2(1H)-quinolone derivatives which are stated to have anti-arrhythmic activity. There is, however, no suggestion in either of these publications that the compounds described therein would be of any benefit in the treatment and/or prevention of psychotic disorders such as schizophrenia, still less that in doing so they might be expected to manifest fewer side-effects than those exhibited by classical neuroleptic agents.

The present invention accordingly provides the use of a compound of formula I, or a pharmaceutically acceptable salt thereof or a prodrug thereof:

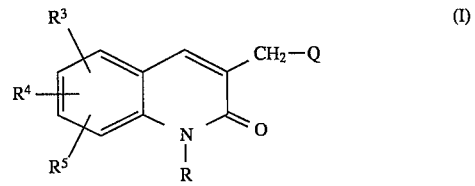

wherein

R represents hydrogen or $C_{1-6}$ alkyl;

Q represents a moiety of formula Qa, Qb, Qc or Qd:

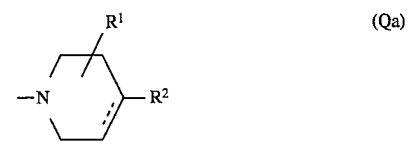

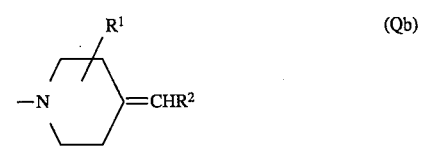

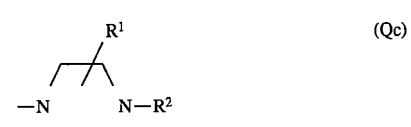

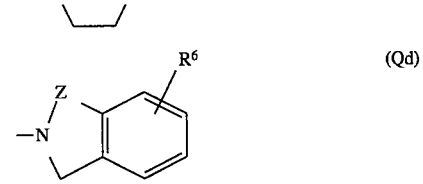

in which the broken line represents an optional chemical bond;

$R^1$ represents hydrogen, or an optionally substituted $C_{1-6}$ alkyl, $C_{1-6}$ alkoxy, $C_{2-6}$ alkenyl, $C_{2-6}$ alkynyl, aryl, aryl($C_{1-6}$)alkyl, aryl($C_{1-6}$)alkoxy, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl, heteroaryl($C_{2-6}$)alkenyl or heteroaryl($C_{2-6}$)alkynyl group;

$R^2$ represents an optionally substituted $C_{1-6}$ alkyl, $C_{1-6}$ alkoxy, $C_{2-6}$ alkenyl, $C_{2-6}$ alkynyl, aryl, aryl($C_{1-6}$)alkyl, aryl($C_{1-6}$)alkoxy, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl, heteroaryl($C_{2-6}$)alkenyl or heteroaryl($C_{2-6}$)alkynyl group;

$R^3$, $R^4$ and $R^5$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$;

Z represents —$CH_2$— or —$CH_2CH_2$—;

$R^6$ represents hydrogen, $C_{1-6}$ alkyl, $C_{1-6}$ alkoxy, aryl, aryl($C_{1-6}$)alkyl or halogen; and $R^a$ and $R^b$ independently represent hydrogen, hydrocarbon or a heterocyclic group; for the manufacture of a medicament for the treatment and/or prevention of psychotic disorders such as schizophrenia.

For use in medicine, the salts of the compounds of formula I will be pharmaceutically acceptable salts. Other salts may, however, be useful in the preparation of the compounds of use in the invention or of their pharmaceutically acceptable salts. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of use in the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl and aryl($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl, heteroaryl($C_{1-6}$)alkyl, heteroaryl($C_{2-6}$)alkenyl and heteroaryl($C_{2-6}$)alkynyl groups.

Suitable alkyl groups within the scope of the term "hydrocarbon" and within the definition of the substituents R, $R^1$, $R^2$ and $R^6$ include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups within the scope of the term "hydrocarbon" and within the definition of the substituents $R^1$ and $R^2$ include straight-chained and branched alkenyl groups containing from 2 to 6 carbon atoms. Typical examples include vinyl and allyl groups.

Suitable alkynyl groups within the scope of the term "hydrocarbon" and within the definition of the substituents $R^1$ and $R^2$ include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups within the scope of the term "hydrocarbon" and within the definition of the substituents $R^1$, $R^2$ and $R^6$ include phenyl and naphthyl.

Particular aryl($C_{1-6}$)alkyl groups within the scope of the term "hydrocarbon" and within the definition of the substituents $R^1$, $R^2$ and $R^6$ include benzyl, naphthylmethyl, phenethyl and phenylpropyl.

A particular aryl($C_{2-6}$)alkenyl group within the scope of the term "hydrocarbon" and within the definition of the substituents $R^1$ and $R^2$ is phenylethenyl.

Suitable heterocycloalkyl groups include azetidinyl, pyrrolidyl, piperidyl, piperazinyl, morpholinyl and tetrahydrofuryl groups.

A particular $C_{3-7}$ heterocycloalkyl($C_{1-6}$)alkyl group within the scope of the expression "a heterocyclic group" and within the definition of the substituents $R^1$ and $R^2$ is tetrahydrofurylethyl.

Suitable heteroaryl groups within the scope of the expression "a heterocyclic group" and within the definition of the substituents $R^1$ and $R^2$ include pyridyl, quinolyl, isoquinolyl, pyridazinyl, pyrimidinyl, pyrazinyl, pyranyl, furyl, benzofuryl, dibenzofuryl, thienyl, benzthienyl, indolyl, indazolyl, imidazolyl, benzimidazolyl, oxadiazolyl and thiadiazolyl groups.

Particular heteroaryl($C_{1-6}$)alkyl groups within the scope of the expression "a heterocyclic group" and within the definition of the substituents $R^1$ and $R^2$ include thienylmethyl, pyridylmethyl, pyrimidinylmethyl and pyrazinylmethyl.

The hydrocarbon and heterocyclic groups, as well as the substituents $R^1$ and $R^2$, may in turn be optionally substituted by one or more groups selected from $C_{1-6}$ alkyl, adamantyl, phenyl, aryl($C_{1-6}$)alkyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, trifluoromethanesulphonyloxy, $-NR^vR^w$, $-NR^vCOR^w$, $-NR^vCO_2R^w$, $-NR^vSO_2R^w$, $-CH_2NR^vSO_2R^w$, $-NHCONR^vR^w$, $-PO(OR^v)(OR^w)$, $-CONR^vR^w$, $-SO_2NR^vR^w$ and $-CH_2SO_2NR^vR^w$, in which $R^v$ and $R^w$ independently represent hydrogen, $C_{1-6}$ alkyl, aryl or aryl($C_{1-6}$)alkyl.

The term "halogen" as used herein includes fluorine, chlorine, bromine and iodine, especially chlorine.

The present invention includes within its scope the use of prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds of use in the invention have at least one asymmetric centre, they may accordingly exist as enantiomers. Where the compounds of use in the invention possess two or more asymmetric centres, they may additionally exist as diastereoisomers. It is to be understood that the use of all such isomers and mixtures thereof is encompassed within the scope of the present invention.

Suitably, the substituent R represents hydrogen or methyl, especially hydrogen.

Suitably, the substituent $R^1$ represents hydrogen.

Suitable values for the substituent $R^2$ include $C_{1-6}$ alkyl, phenyl, halophenyl, $C_{1-6}$ alkylphenyl, $C_{1-6}$ alkoxyphenyl, nitrophenyl, benzyl, halobenzyl, phenethyl and phenylethenyl. Particular values of $R^2$ include methyl, ethyl, n-propyl, isopropyl, phenyl, chlorophenyl, ethylphenyl, methoxyphenyl, nitrophenyl, benzyl, chlorobenzyl, phenethyl and phenylethenyl.

Suitable values for the substituents $R^3$, $R^4$ and $R^5$ include hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, fluoro, chloro, methyl, methoxy and benzyloxy.

Particular values of $R^6$ include hydrogen, phenyl, chloro and bromo.

A particular sub-class of compounds of use in the invention is represented by the compounds of formula IIA, and pharmaceutically acceptable salts thereof and prodrugs thereof:

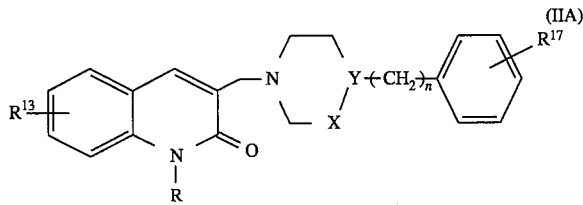

(IIA)

wherein

R is as defined with reference to formula I above;

n is zero, 1, 2 or 3;

—X—Y— represents —CH$_2$—CH—, —CH=C— or —CH$_2$—N—; and

R$^{13}$ and R$^{17}$ independently represent hydrogen, halogen, cyano, nitro, trifluoromethyl, amino, C$_{1-6}$ alkylamino, di (C$_{1-6}$)alkylamino, C$_{1-6}$ alkyl, C$_{1-6}$ alkoxy, aryl(C$_{1-6}$)alkoxy or C$_{2-6}$ alkylcarbonyl.

Particular values of R$^{13}$ include hydrogen, fluoro, chloro, methyl, ethyl, methoxy and benzyloxy.

Particular values of R$^{17}$ include hydrogen, chloro, methoxy and nitro.

Another sub-class of compounds of use in the invention is represented by the compounds of formula IIB, and pharmaceutically acceptable salts thereof and prodrugs thereof:

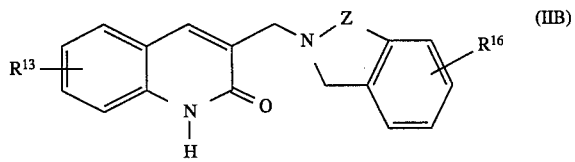

(IIB)

wherein

Z represents —CH$_2$— or —CH$_2$CH$_2$—;

R$^{13}$ is as defined with reference to formula IIA above; and

R$^{16}$ represents hydrogen, C$_{1-6}$ alkyl, C$_{1-6}$ alkoxy, aryl, aryl(C$_{1-6}$)alkyl or halogen.

Particular values of R$^{16}$ include hydrogen, phenyl, chloro and bromo, especially hydrogen.

A further sub-class of compounds of use in the invention is represented by the compounds of formula IIC, and pharmaceutically acceptable salts thereof and prodrugs thereof:

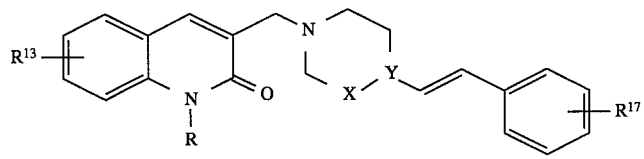

(IIC)

wherein

R is as defined with reference to formula I above; and

X, Y, R$^{13}$ and R$^{17}$ are as defined with reference to formula IIA above.

Specific compounds of use in the present invention include: 3-(4-phenylpiperazin-1-ylmethyl)-2(1H)-quinolone; and pharmaceutically acceptable salts thereof and prodrugs thereof.

Certain compounds falling within the definition of formula I above are novel. Particular sub-classes of novel compounds in accordance with the present invention comprise the compounds of formula IIB and IIC as defined above; the compounds of formula IIA as defined above wherein n is zero and —X—Y— represents —CH=C—; the compounds of formula IIA as defined above wherein n is zero, —X—Y— represents —CH$_2$—N— and R is other than hydrogen; and salts and prodrugs thereof. The invention further provides a novel compound selected from the following:

3-[4-(4-chlorophenyl)piperazin-1-ylmethyl]-2(1H)-quinolone;

3-[4-(4-methoxyphenyl)piperazin-1-ylmethyl]-2(1H)-quinolone;

3-(1,2,3,4-tetrahydroisoquinolin-2-ylmethyl)-2(1H)-quinolone;

3-(4-phenyl-1,2,3,6-tetrahydropyrid-1-ylmethyl)-2(1H)-quinolone;

3-[4-(2-phenylethyl)-1,2,3,6-tetrahydropyrid-1-ylmethyl]-2(1H)-quinolone;

3-(4-benzyl-1,2,3,6-tetrahydropyrid-1-ylmethyl)-2(1H)-quinolone;

1-methyl-3-(4-phenylpiperazin-1-ylmethyl)-2(1H)-quinolone;

3-[4-(2-phenylethenyl)-1,2,3,6-tetrahydropyrid-1-ylmethyl]-2(1H)-quinolone;

and salts and prodrugs thereof.

The invention also provides pharmaceutical compositions comprising one or more of the novel compounds according to the invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present-invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I above, including the novel compounds according to the present invention, may be prepared by a process which comprises reacting a compound of formula III with a compound of formula IV:

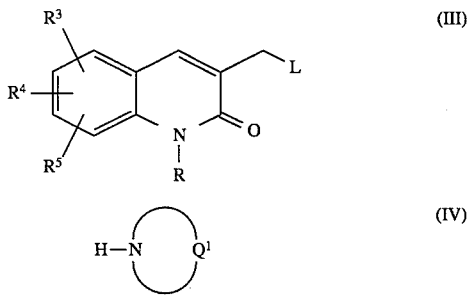

wherein R, $R^3$, $R^4$ and $R^5$ are as defined above, $Q^1$ represents the residue of a moiety of formula Qa to Qd as defined above, and L represents a suitable leaving group.

The leaving group L is suitably a halogen atom, e.g. chlorine or bromine.

The reaction is conveniently carried out by stirring the reactants under basic conditions in a suitable solvent, for example potassium carbonate in N,N-dimethylformamide, or triethylamine in tetrahydrofuran or acetonitrile.

Where they are not commercially available, the starting materials of formula III and IV may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art. For example, a compound of formula I wherein R is hydrogen initially obtained may be converted into a compound of formula I wherein R represents $C_{1-6}$ alkyl by standard alkylation techniques, such as by treatment with an alkyl iodide, e.g. methyl iodide, typically under basic conditions, e.g. sodium hydride in dimethylformamide, or triethylamine in acetonitrile.

Where the above-described processes for the preparation of the compounds of use in the invention give rise to mixtures of stereoisomers, these isomers may be separated by conventional techniques, such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid)at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mMTris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine $D_4$ receptor subtype of below 1.5 μM.

EXAMPLE 1

3-(4-Phenylninerazin-1-yl)methylquinol-2(1H)-one

3-Bromomethylquinolin-2(1H)-one (480 mg, 2 mmol), (prepared according to the method of M. Uchida et al, *Chem. Pharm. Bull.*, 1985, 33, 3775), 1-phenylpiperazine (324 mg, 2 mmol), and triethylamine (303 mg, 3 mmol) were combined in dry tetrahydrofuran (20 ml)and the mixture stirred under reflux for 3 h. The residue remaining on removal of solvent was suspended in water and the suspension filtered, the collected solid washed with water and methanol, dried and recrystallised from dioxan to give the product as a buff powder (391 mg), m.p. 260° C. (dec.); (Found: C, 75.07; H, 6.82; N, 12.95. $C_{20}H_{21}N_3O$ requires C, 75.21; H, 6.63; N, 13.16%); $\delta_H$ (DMSO-$d_6$) 2.60–2.63 (4H, m, 2×piperazinyl CH$_2$), 3.17–3.19 (4H, m, 2×piperazinyl CH$_2$), 3.47 (2H, s, C$\underline{H}_2$NR$_2$), 6.77 (1H, t, J 7.2 Hz, 4'-H), 6.93(2H, d, J 8.0 Hz, 2', 6'-H), 7.15–7.23 (3H, m, 6-H and 3', 5'-H), 7.31 (1H, d, J 8.1 Hz, 5-H), 7.46 (1H, t, J 8.3 Hz, 7-H), 7.69 (1H, d, J 7.2 Hz, 8-H), 7.90 (1H, s, 4-H), and 11.79 (1H, br s, NH); m/z (CI$^+$, NH$_3$) 320 (M+1)$^+$.

Similarly prepared were:

EXAMPLE 2

3-(4-[4-Methoxyphenyl]piperazin-1-yl) methylquinolin-2(1H)-one

M.p. 263°–266° C. (dioxan/H$_2$O); (Found: C, 71.74; H, 6.72; N, 11.55. $C_{21}H_{23}N_3O_2$.0.1H$_2$O requires C, 71.81; H, 6.66; N, 11.96%); $\delta_H$(DMSO-$d_6$) 2.61 (4H, br s, 2×piperazinyl CH$_2$), 3.06 (4H, br s, 2×piperazinyl CH$_2$), 3.46 (2H, s, C$\underline{H}_2$NR$_2$), 3.68 (3H, s, OCH$_3$), 6.81 (2H, d, J 9.2 Hz, ArH), 6.89 (2H, d, J 9.2 Hz, ArH), 7.16 (1H, t, J 8.0 Hz, ArH), 7.30 (1H, d, J 8.0 Hz, ArH), 7.45 (1H, t, J 8.3 Hz, ArH), 7.68 (1H, d, J 6.9 Hz, ArH), 7.88 (1H, s, 4-H), and 11.76 (1H, br s, NH); m/z (CI$^+$, NH$_3$) 350(M+1)$^+$.

EXAMPLE 3

3-(1,2,3,4-Tetrahydroquinolin-2-yl) methylquinolin-2(1H)-one

M.p. 196°–199° C. (dioxan); (Found: C, 77.52; H, 6.35; N, 9.37. $C_{19}H_{18}N_2O$.0.25H$_2$O requires C, 77.39; H, 6.32; N, 9.50%); $\delta_H$ (DMSO-$d_6$) 2.74–2.77 (2H, m,—C$\underline{H}_2$), 2.86–2.89 (2H, m, —C$\underline{H}_2$), 3.57(2H, s, 3—C$\underline{H}_2$NR$_2$), 3.66 (2H, s, R$_2$NC$\underline{H}_2$Ar), 7.03–7.18 (5H, m, ArH), 7.31 (1H, d, J 8.3 Hz, 5-H), 7.46 (1H, ddd, J 9.5, 8.4, 1.5 Hz, 7-H), 7.68 (1H, d, J 7.8 Hz, 8-H), 7.92 (1H, s 4-H), and 11.80 (1H, br s, NH); m/z (CI$^+$, NH$_3$) 291 (M+1)$^+$.

EXAMPLE 4

3-(4-[4-Chlorophenyl]piperazin-1-yl)methyl-1H-quinolin-2-one

M.p. 256°–259° C. (dioxan/H$_2$O); (Found: C, 68.09; H, 5.61; N, 11.91; $C_{20}H_{20}ClN_3O$ requires C, 67.87; H, 5.70; N, 11.88%); $\delta_H$ (DMSO-$d_6$) 2.59–2.61 (4H, m, piperazinyl H), 3.16–3.19 (4H, m, piperazinyl H), 3.46 (2H, s, NC$\underline{H}_2$Ar), 6.94 (2H, d, J 9.1 Hz, ArH), 7.14–7.24 (3H, m, ArH), 7.31 (1H, d, J 8.2 Hz, ArH), 7.46 (1H, t, J 8.1 Hz, ArH), 7.68 (1H, d, J 7.0 Hz, ArH), 7.88 (1H, s, ArH), and 11.77 (1H, br s, NH); m/z (CI$^+$, NH$_3$) 354 (M+1)$^+$.

EXAMPLE 5

3-(4-Phenyl-1,2,3,6-tetrahydronyridin-1-yl) methyl-2(1H)-quinolone

M.p. 213°–216° C. (dioxan/H$_2$O); (Found: C, 80.26; H, 6.58; N, 9.03. $C_{21}H_{20}N_2O$ requires C, 79.72; H, 6.37; N, 8.85%). $\delta_H$ (DMSO-$d_6$) 2.54 (2H, br s, tetrahydropyridinyl 3-CH$_2$), 2.73 (2H, t, J 5.5 Hz, tetrahydropyridinyl 2-CH$_2$), 3.20 (2H, br s, tetrahydropyridinyl 6-CH$_2$), 3.52 (2H, s, NC$\underline{H}_2$Ar), 6.19 (1H, br s, tetrahydropyridinyl 5-CH), 7.16 (1H, t, J 7.0 Hz, ArH), 7.24 (1H, t, J 7.3 Hz, ArH), 7.29–7.35 (3H, m, ArH), 7.43–7.48 (3H, m, ArH), 7.69 (1H, d, J 6.4 Hz, 8-H), 7.90 (1H, s, 4-H), and 11.78 (1H, br s, NH); m/z (CI$^+$, NH$_3$) 317 (M+1)$^+$.

EXAMPLE 6

3-(4-Phenylethyl-1,2,3,6-tetrahydropyridin-1-yl) methyl-2-(1H)-quinolone

M.p. 177°–179° C. (MeOH/H$_2$O); (Found: C, 79.31; H, 6.99; N, 8.05. $C_{23}H_{24}N_2O$. 0.15H$_2$O requires C, 79.56; H, 7.05; N, 8.07%); $\delta_H$ (DMSO-$d_6$) 2.11 (2H, br s, tetrahydropyridinyl 3-CH$_2$), 2.23 (2H, t, J 7.6 Hz, PhCH$_2$C$\underline{H}_2$), 2.55 (2H, t, J 5.6 Hz, tetrahydropyridinyl 2-CH$_2$), 2.67–2.73 (2H, m, tetrahydropyridinyl 6-CH$_2$), 3.44 (2H, s, NC$\underline{H}_2$Ar), 5.40 (1H, br s, tetrahydropyridinyl 5-CH), 7.14–7.30 (7H, m, ArH), 7.45 (1H, t, J 7.0 Hz, ArH), 7.68 (1H, d, J 7.2 Hz, 8-H), 7.84 (1H, s, 4-H), and 11.76 (1H, br s, NH); m/z (CI$^+$, NH$_3$) 345 (M+1)$^+$.

EXAMPLE 7

3-(4-Benzyl-1,2,3,6-tetrahydropyridin-1-yl) methyl-2(1H)-quinolone

M.p. 155°–158° C. (DMF/H$_2$O); (Found: C, 79.77; H, 6.77; N, 8.53. $C_{22}H_{22}N_2O$ requires C, 79.97; H, 6.71; N, 8.48%); $\delta_H$ (DMSO-$d_6$) 1.99 (2H, br s, tetrahydropyridinyl 3-CH$_2$), 2.53 (2H, br s, tetrahydropyridinyl 2-CH$_2$), 2.89 (2H, br s, tetrahydropyridinyl 6-CH$_2$), 3.27 (2H, s, PhC$\underline{H}_2$), 3.43 (2H, s, NC$\underline{H}_2$Ar), 5.42 (1H, br s, tetrahydropyridinyl 5-CH), 7.12–7.21 (4H, m, ArH), 7.27–7.31 (3H, m, ArH), 7.44 (1H, t, J 7.1 Hz, ArH), 7.67 (1H, d, J 7.0 Hz, 8-H), 7.82 (1H, s, 4-H), and 11.75 (1H, br s, NH); m/z (CI$^+$, NH$_3$) 331 (M+1)$^+$.

EXAMPLE 8

(E)-3-(4-[2-Phenylethenyl]-1,2,3,6-tetrahydropyridin-1-yl)methyl-2(1H)-quinolone M.p. 258°–260° C. (DMF); (Found: C, 80.47; H, 6.44; N, 8.21. $C_{23}H_{22}N_2O$ requires C, 80.67; H, 6.48; N, 8.18%); $\delta_H$ (DMSO-$d_6$) 2.39 (2H, br s, tetrahydropyridinyl CH$_2$), 2.68 (2H, t, J 5.6 Hz, tetrahydropyridinyl CH$_2$), 3.17 (2H, br s, tetrahydropyridinyl CH$_2$), 3.51 (2H, s, ArCH$_2$N), 5.94 (1H, br s, tetrahydropyridinyl 5-H), 6.50 (1H, d, J 16.2 Hz, C$\underline{H}$=CH), 6.92 (1H, d, J 16.2 Hz, CH=C$\underline{H}$), 7.14–7.23 (2H, m, ArH), 7.29–7.35 (3H, m, ArH), 7.43–7.49 (3H, m, ArH), 7.70 (1H, d, J 7.9 Hz, ArH), 7.89 (1H, s, 4-H), and 11.78 (1H, br s, NH); m/z (CI$^+$, NH$_3$) 343 (M+1)$^+$.

We claim:

1. A method for the treatment of schizophrenia which comprises administering to a patient in need thereof a compound of formula I, or a pharmaceutically acceptable salt thereof or a prodrug thereof:

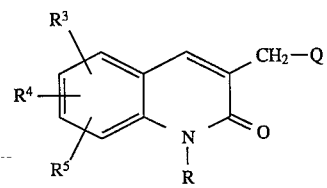

wherein

R represents hydrogen or $C_{1-6}$ alkyl;

Q represents a moiety of formula Qa, Qb, Qc or Qd:

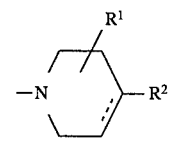
(Qa)

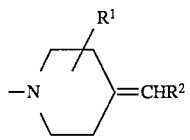
(Qb)

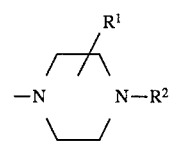
(Qc)

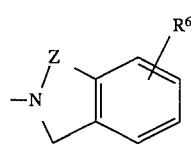
(Qd)

in which the broken line represents an optional chemical bond;

$R^1$ represents hydrogen, or an optionally substituted $C_{1-6}$ alkyl, $C_{1-6}$ alkoxy, $C_{2-6}$ alkenyl, $C_{2-6}$ alkynyl, aryl, aryl($C_{1-6}$)alkyl, aryl($C_{1-6}$)alkoxy, aryl($C_{2-6}$)alkenyl, or aryl($C_{2-6}$)alkynyl;

$R^2$ represents an optionally substituted $C_{1-6}$ alkyl, $C_{1-6}$ alkoxy, $C_{2-6}$ alkenyl, $C_{2-6}$ alkynyl, aryl, aryl($C_{1-6}$)alkyl, aryl($C_{1-6}$)alkoxy, aryl($C_{2-6}$)alkenyl, or aryl($C_{2-6}$)alkynyl;

$R^3$, $R^4$ and $R^5$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$;

z represents —$CH_2$— or —$CH_2CH_2$—;

$R^6$ represents hydrogen, $C_{1-6}$ alkyl, $C_{1-6}$ alkoxy, aryl, aryl($C_{1-6}$)alkyl or halogen; and $R^a$ and $R^b$ independently represent hydrogen, or hydrocarbon.

2. A method for the treatment of schizophrenia which comprises administering to a patient in need thereof a compound represented by formula IIA, or pharmaceutically acceptable salt thereof or prodrug thereof:

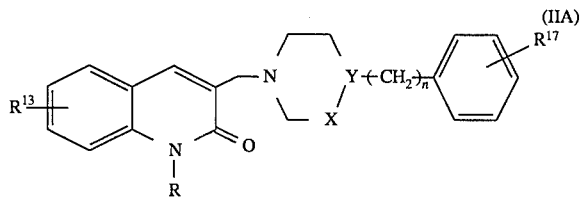
(IIA)

wherein
R is as defined in claim 1;
n is zero, 1, 2 or 3;
—X—Y— represents —$CH_2$—CH—, —CH=C— or —$CH_2$—N—; and
$R^{13}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

3. The method as claimed in claim 1 wherein the compound is selected from:
3-(4-phenylpiperazin-1-ylmethyl)-2(1H)-quinolone; a pharmaceutically acceptable salt or prodrug thereof.

4. A compound of formula IIA

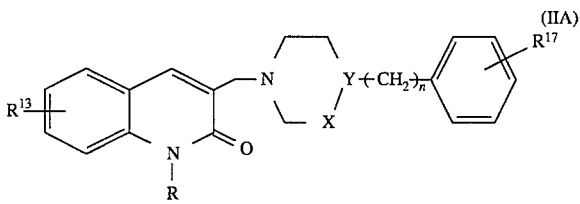
(IIA)

wherein
R represents hydrogen or $C_{1-6}$ alkyl;
n is zero
—X—Y— represents —CH=C— and
$R^{13}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl or a pharmaceutically acceptable salt or prodrug thereof.

5. A compound of formula IIA

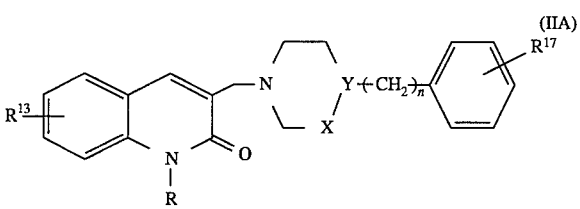
(IIA)

wherein
n is zero,
—X—Y— represents —$CH_2$—N—;
R represents $C_{1-6}$ alkyl, and
$R^{13}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl, or a pharmaceutically acceptable salt or prodrug thereof.

6. A compound of formula IIB, or a salt thereof or a prodrug thereof:

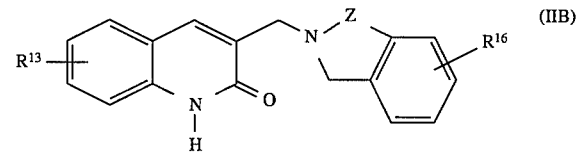
(IIB)

wherein
Z represents —$CH_2$— or —$CH_2CH_2$—;
$R^{13}$ is as defined in claim 2; and
$R^{16}$ represents hydrogen, $C_{1-6}$ alkyl, $C_{1-6}$ alkoxy, aryl, aryl($C_{1-6}$)alkyl or halogen.

7. A compound of formula IIC, or a pharmaceutically acceptable salt or a prodrug thereof:

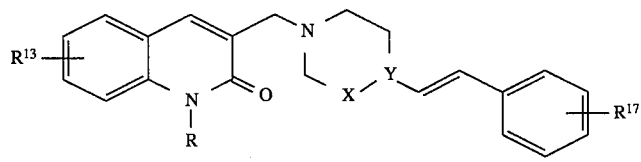

wherein

R is hydrogen or $C_{1-6}$alkyl;

—X—Y— represents —$CH_2$—CH—, —CH=C or —$CH_2$—N—; and $R^{13}$ and $R^{17}$ independently represent hydrogen, halogen, cyano, nitro, trifluoromethyl, amino, $C_{1-6}$ alkylamino, di($C_{1-6}$)alkylamino, $C_{1-6}$alkyl, $C_{1-6}$ alkoxy, aryl ($C_{1-6}$)alkoxy or $C_{2-6}$ alkylcarbonyl.

8. A compound selected from:

3-[4-(4-chlorophenyl)piperazin-1-ylmethyl]-2(1H)-quinolone;

3-[4-(4-methoxyphenyl)piperazin-1-ylmethyl]-2(1H)-quinolone;

3-(1,2,3,4-tetrahydroisoquinolin-2-ylmethyl)-2(1H)-quinolone;

3-(4-phenyl-1,2,3,6-tetrahydropyrid-1-ylmethyl)-2(1H)-quinolone;

3-[4-(2-phenylethyl)-1,2,3,6-tetrahydropyrid-1-ylmethyl]-2(1H)-quinolone;

3-(4-benzyl-1,2,3,6-tetrahydropyrid-1-ylmethyl)-2(1H)-quinolone;

1-methyl-3-(4-phenylpiperazin-1-ylmethyl)-2(1H)-quinolone;

3-[4-(2-phenylethenyl)-1,2,3,6-tetrahydropyrid-1-ylmethyl]- 2(1H)-quinolone;

or a pharmaceutically acceptable salt or prodrug thereof.

9. A pharmaceutical composition comprising a compound as claimed in claim 8 in association with a pharmaceutically acceptable carrier.

10. A method for the treatment of schizophrenia which comprises administering to a patient in need of such treatment an effective amount of a compound as claimed in claim 9.

11. A pharmaceutical composition comprising a compound as claimed in claim 5 in association with a pharmaceutically acceptable carrier.

12. A pharmaceutical composition comprising a compound as claimed in claim 6 in association with a pharmaceutically acceptable carrier.

13. A pharmaceutical composition comprising a compound as claimed in claim 7 in association with a pharmaceutically acceptable carrier.

14. A pharmaceutical composition comprising a compound as claimed in claim 8 in association with a pharmaceutically acceptable carrier.

15. A method for the treatment of schizophrenia which comprises administering to a patient in need thereof an effective amount of a compound as claimed in claim 5.

16. A method for the treatment of schizophrenia which comprises administering to a patient in need thereof an effective amount of a compound as claimed in claim 6.

17. A method for the treatment of schizophrenia which comprises administering to a patient in need thereof an effective amount of a compound as claimed in claim 7.

18. A method for the treatment of schizophrenia which comprises administering to a patient in need thereof an effective amount of a compound as claimed in claim 8.

* * * * *